United States Patent [19]

Amrein et al.

[11] Patent Number: 4,906,626

[45] Date of Patent: Mar. 6, 1990

[54] METHOD OF USE FOR TREATMENT OR PREVENTION OF COGNITIVE DISORDERS

[75] Inventors: Roman Amrein, Bettingen; Ravi Anand, Basel, both of Switzerland

[73] Assignee: Hoffman-La Roche Inc., Nutley, N.J.

[21] Appl. No.: 297,168

[22] Filed: Jan. 13, 1989

[30] Foreign Application Priority Data

Jan. 28, 1988 [CH] Switzerland ............... 298/88

[51] Int. Cl.⁴ ........................... A61K 31/535
[52] U.S. Cl. ................................ 514/237.8
[58] Field of Search ........................ 514/234

Primary Examiner—Stanley J. Friedman
Attorney, Agent, or Firm—George M. Gould; Bernard S. Leon; William G. Isgro

[57] ABSTRACT p-Chloro-N-(2-morpholinoethyl)benzamide is capable of counteracting cognitive disorders and can accordingly be used in the treatment or prevention of cognitive disorders, especially of those which are caused by old age.

6 Claims, No Drawings

METHOD OF USE FOR TREATMENT OR PREVENTION OF COGNITIVE DISORDERS

BRIEF SUMMARY OF THE INVENTION

The invention relates to a method of treating or preventing cognitive disorders utilizing p-chloro-N-(2-morpholinoethyl)benzamide.

DETAILED DESCRIPTION OF THE INVENTION

In accordance with the invention, it has been found that p-chloro-N-(2-morpholinoethyl)benzamide (referred to hereinafter as moclobemide) of the formula

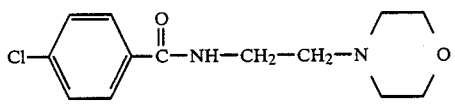

is capable of counteracting cognitive disorders. Moclobemide is a reversible MAO-A inhibitor used for the treatment of depressive states. In this connection, reference is made to the following patent specifications and literature references: German Offenlegungsschrift No. 2 706 179; U.S. Pat. No. 4 210 754; Pharmacopsychiat., 17, (1984), 122-125; J. Pharm. and Pharmacol., Vol. 36, Suppl., November 1984, 64 W; and Acta Therapeutica, 11, (1985), 249-251.

It is evident from the last-mentioned literature reference that moclobemide has been used for the treatment of depressions in geriatric patients with dementia caused by old age, whereby in all patients a reasonable or even substantial improvement in the symptoms of depression was achieved. The fact that the symptoms of depression could be abated completely in only a few cases is explained by the authors as a probable persistence of the dementia. It has now however surprisingly been found that cognitive disorders can successfully be treated or prevented by the administration of moclobemide. The invention is based on the just-mentioned finding and is accordingly concerned with the use of moclobemide in the treatment or prevention of cognitive disorders, especially those caused by old age. Examples of such disorders are hypomnesis caused by old age, primary and secondary degenerative dementia, for example dementia of the Alzheimer type or multi-infarct caused dementia, and cerebrovascular disorders and consequences of strokes.

In the treatment or prevention of the above-mentioned disorders, moclobemide can be administered systemically, preferably enterally, particularly orally.

The dosage varies in accordance with the requirements of the individual patient as determined by the attending practitioner. In general, however, a daily dosage in the range of from about 0.1 mg to about 20 mg, preferably from about 1 mg to about 10 mg, per kg body weight of the patient can be used. The dosage can be administered in a single dose or in several partial doses divided in accordance with a dosage plan as determined by the praticitioner according to the requirements of the patient.

As dosage forms, there come into consideration for systemic administration usual solid or liquid dosage forms, for example, suppositories or, as solid oral dosage forms, capsules, tablets, coated tablets, dragees, pills, powders, granulates and the like, as liquid oral dosage forms solutions, syrups, suspensions, elixirs and the like and as parenteral dosage forms, infusion or injection solutions, which can be injected intravenously or intramuscularly.

According to the present invention, moclobemide can be incorporated in the enteral or parenteral dosage form in any effective amount which is suitable for the administration. It is, however, preferred to prepare dosage forms which contain the active substance moclobemide in an amount of from about 5 mg to about 500 mg, preferably of from about 50 mg to about 200 mg. Capsules and coated tablets are especially preferred.

The preparation of the above-mentioned dosage forms can be effected in the usual manner, for example, as set forth in the following Examples.

EXAMPLE 1

Coated tablets containing the following ingredients can be prepared:

| Ingredients | mg/coated tablet |
|---|---|
| 1. Moclobemide | 50.0 |
| 2. Powdered lactose | 74.0 |
| 3. Maize Starch | 60.0 |
| 4. Polyvinylpyrrolidone | 10.0 |
| 5. Sodium carboxymethyl-starch | 5.0 |
| 6. Magnesium stearate | 1.0 |
| Total | 200.0 |

Procedure:

(a) Preparation of the uncoated tablets

The moclobemide is mixed with the powdered lactose, the maize starch and the polyvinylpyrrolidone and sieved. The powder mixture is moistened with deionized water and kneaded. The resulting mass is granulated, dried and sieved. The granulate is mixed with the sieved sodium carboxymethyl-starch and the sieved magnesium stearate and then pressed into tablets.

(b) Coating of the tablets 2.5 mg of hydroxypropylmethylcellulose are dissolved in 25 mg of deionized water. An aqueous (10 mg) suspension of 1.88 mg of talc, 0.5 mg of titanium dioxide, 0.1 mg of yellow iron oxide and 0.02 mg of red iron oxide is stirred into this solution. The coating suspension is sprayed on the tablets and the coated tablets are dried at 45° C. overnight. The total weight of a coated tablet is 205.0 mg.

EXAMPLE 2

Coated tablets containing the following ingredients can be prepared:

| Ingredients | mg/coated tablet |
|---|---|
| 1. Moclobemide | 100.0 |
| 2. Powdered lactose | 148.0 |
| 3. Maize starch | 120.0 |
| 4 Polyvinylpyrrolidone | 20.0 |
| 5. Sodium carboxymethyl-starch | 10.0 |
| 6. Magnesium stearate | 2.0 |
| Total | 400.0 |

Procedure:

(a) Preparation of the uncoated tablets

The moclobemide is mixed with the powdered lactose, the maize starch and the polyvinylpyrrolidone and sieved. The powder mixture is moistened with deionized water and kneaded. The resulting mass is granulated, dried and sieved. The granulate is mixed with the sieved sodium carboxymethyl-starch and the sieved magnesium stearate and then pressed into tablets.

(b) Coating of the tablets 5 mg of hydroxypropylmethylcellulose are dissolved in 50 mg of deionized water. An aqueous (20 mg) suspension of 3.76 mg of talc, 1.0 mg of titanium dioxide, 0.2 mg of yellow iron oxide and 0.04 mg of red iron oxide is stirred into this solution. The coating suspension is sprayed on to the tablets and the coated tablets are dried at 45° C. overnight. The total weight of a coated tablet is 410.0 mg.

EXAMPLE 3

Coated tablets containing the following ingredients can be prepared:

| Ingredients | mg/coated tablet |
| --- | --- |
| 1. Moclobemide | 150.0 |
| 2. Powdered lactose | 148.0 |
| 3. Maize starch | 60.0 |
| 4. Polyvinylpyrrolidone | 25.0 |
| 5. Sodium carboxymethyl-starch | 15.0 |
| 6. Magnesium stearate | 2.0 |
| Total | 400.0 |

Procedure:

(a) Preparation of the uncoated tablets

The moclobemide is mixed with the powdered lactose, the maize starch and the polyvinylpyrrolidone and sieved. The powder mixture is moistened with deionized water and kneaded. The resulting mass is granulated, dried and sieved. The granulate is mixed with the sieved sodium carboxymethyl-starch and the sieved magnesium stearate and then pressed into tablets.

(b) Coating of the tablets 4.5 mg of hydroxypropylmethylcellulose are dissolved in 55 mg of deionized water together with 0.6 mg of polyethylene glycol. An aqueous (41 mg) suspension of 2.4 mg of talc, 2.9 mg of titanium dioxide and 0.1 mg of yellow iron oxide is stirred into this solution. After adding 1.5 mg of ethylcellulose dispersion, the coating suspension is obtained which is sprayed on to the tablets. The coated tablets are dried at 45° C. overnight. The total weight of a coated tablet is 412.0 mg.

Example 4

Sachets containing the following ingredients can be prepared:

| Ingredients | mg/sachet |
| --- | --- |
| 1. Moclobemide | 400.0 |
| 2. Powdered lactose | 1870.0 |
| 3. Maize starch | 680.0 |
| 4. Polyvinylpyrrolidone | 50.0 |
| Total | 3000.0 |

Procedure:

The above-mentioned ingredients are mixed. The mixture is moistured with about 800 mg of water and the resulting mass is granulated, dried and sieved.

EXAMPLE 5

Hard gelatin capsules containing the following ingredients can be prepared:

| Ingredients | mg/capsule |
| --- | --- |
| 1. Moclobemide | 200.0 |
| 2. Powdered lactose | 162.0 |
| 3. White maize starch | 100.0 |
| 4. Polyvinylpyrrolidone | 8.0 |
| 5. Talc | 9.0 |
| 6. Magnesium stearate | 1.0 |
| Total | 480.0 |

Procedure:

The moclobemide is mixed with the powdered lactose, the maize starch and the polyvinylpyrrolidone. The mixture is moistened with deionized water and kneaded. The resulting mass is granulated, dried and sieved. The granulate obtained is mixed with the talc and the magnesium stearate and the powder obtained is filled into interlocking capsules.

The therapeutic and prophylactic activity of moclobemide in cognitive disorders was demonstrated in the following tests:

(A) The activity of moclobemide in inhibiting cerebral insufficiency was determined according to the following procedure on female albino rats (Füllinsdorf/Switzerland). The test apparatus is a Skinner box with an electrifiable grid floor and a grey quadrangular platform in one corner. Untrained female rats weighing 100–120 g are placed individually on the platform. As soom as they descend to the grid floor they receive an electric foot shock (0.8 mA). The normal reaction of untrained rats is to jump back on to the platform. However, since the rats always try to climb down again, the foot shock procedure must be repeated several times for each animal. After these several repetitions per animal, the rats have learnt a so-called "passive avoidance response", that is, they no longer try to descend to the grid floor because they know that they will be punished with an electric shock.

Immediately, thereafter, the rats are divided into groups of at least 15 animals each. The first group receives an injection (s.c.) of 1 mg/kg of scopolamine hydrobromide as well as an oral dosage of the carrier material, while the remaining groups receive an injection (s.c.) of 1 mg/kg scopolamine hydrobromide and different oral dosages of moclobemide.

Two hours later, each rat is placed once on the platform in the Skinner box. The criterion for the evaluation of this test to determine the activity of a preparation on short-term memory is whether or not the animal remains on the platform for about 30 seconds (the result can thus read for each animal only "yes" or "no"). The statistical significance of the difference between the results obtained with the first and the remaining groups is determined by means of the Chi-Square test. A dosage of moclobemide is denoted as active when the number of positive results ("yes") is significantly different from that in the control animals treated with scopolamine hydrobromide (1 mg/kg s.c.) and only placebo (p.o.).

In this test, oral dosages of 0.1, 0.3 and 1 mg/kg of moclobemide bring about a significant increase in the positive results when compared to the results in the control animals treated with scopolamine hydrobromide and only placebo.

(B) In order to investigate the activity on the long-term memory, the test procedure described above is carried out with the following two variations. Firstly, 3 mg/kg of cycloheximide are administered subcutaneously to the test animals in place of 1 mg/kg of scopolamine hydrobromide and, secondly, the evaluation in order to determine the activity of a preparation is not done until 48 hours later.

In this test, moclobemide exhibits a significant activity in an oral dosage of 1 mg/kg.

The above results determined in the animal test can be confirmed in the human experimental trial described hereinafter, which was carried out in conformity with the Declaration of Helsinki, in the version of Venice.

Twenty-nine (29) young, healthy, normal male volunteers, who prior to the trial had given their written agreement thereto, completed this study. In order that no volunteer suffer a health risk, each was selected according to extremely strict criteria. Moreover, during the trial each volunteer was subjected to a thorough medical examination, including determination of the haematological values, a biochemical analysis of blood and urine as well as an EEG. Since the test substance is a MAO inhibitor, a strict diet was imposed on the volunteers at all stages of the trial as well as on the previous and following days. Each volunteer was required at weekly intervals during trial to change in each case to a different substance being tested. After completion of the trial, all volunteers were again subjected to a further thorough medical examination.

In order to evaluate the impairment of cognitive capacity after administration of scopolamine as well as its possible improvement after subsequent administration of the test compounds, a battery of psychometric tests was compiled, which consisted essentially of the following sub-tests (all procedures used in this case have shown themselves to be sensitive with respect to scopolamine):

1. "Buschke-Fuld Selective Reminding Task" (Buschke and Fuld, Neurology, 1974, 24, 1019–1025). This procedure has proved to be sensitive for evaluating the cognitive deficit in Alzheimer patients and reflects their deficit (Ober et al., Brain and Cognition 1985, 4, 90–103).

2. "Number joining test (Trail Making Task)" (Reitan, Perceptual and Motor Skills 1958, 8, 71–76; Oswald and Fleischmann, Nürnberger Altersinventar 1986). This is a procedure to evaluate special visuomotoric coordination capacity as well as attentiveness. Even in patients with organically-caused strokes, this test has proved to be especially sensitive in evaluating the loss of performance.

3. "Choice reaction times (Choice Reaction Time)" have been used for many years again and again to investigate the influence of medicaments on psychomotoric performance (e.g. Hindmarch, Brit. J. Clin. Pharmac. 1979, 8, 43S–46S). The reaction times represent a good measurement of general cognitive capacity.

4. "Sternberg Memory Scanning" (Sternberg, Q. J. of Exp. Psychol., 1975, 27, 1–32) is also a medicament-sensitive procedure (Subhan and Hindmarch, Neuropsychobiology 1984, 12, 244–248) for evaluating short-term memory capacity.

5. "Rapid Visual Information Processing Task" (for example, Wesnes and Warburton, Psychopharmacology, 1984, 82, 147–150) is a medicament-sensitive procedure and is used to measure long-term concentration capacity.

Before the beginning of the study, the volunteers were able to practice parallel forms of the battery of tests to evaluate cognitive performance and carried them out as required at least on three occasions. The volunteers were required not to smoke and to take no caffeine-containing drinks 12 hours before the respective trial day until the data gathering had been concluded.

The trial began only after the volunteers first completed the battery of tests without the administration of any substance in order to obtain the base values. The base values were then compared with the values obtained 60 minutes after administration of the scopolamine in order to establish the degree of impairment induced by scopolamine. A requirement was that the impairment of memory in the Buschke-Fuld Test induced by scopolamine was to be at least 30% 60 minutes after the administration of scopolamine with respect to the recall from the long-term memory.

After determining the base value, 0.7 mg of scopolamine hydrochloride was injected subcutaneously into each volunteer. Sixty (60) minutes later the volunteer was again required to perform the battery of tests in order to establish the impairment induced by scopolamine. Ninety-five (95) minutes after the scopolamine injection, a test substance in 400 ml of orange juice was administered orally to the volunteers. The test substances were 1500 mg of aniracetam, 750 mg, 1500 mg and, respectively, 3000 mg of 3-hydroxyaniracetam, 400 mg of moclobemide or placebo. One Hundred and Twenty (120) minutes after the scopolamine injection, the volunteers were again required to complete the battery of tests.

For each sub-test, the values obtained 60 minutes after the scopolamine injection were taken as the base values. In the case of each volunteer, this value was subtracted from the corresponding value which was obtained 120 minutes after the scopolamine injection, that is, 35 minutes after the administration of a test substance. The difference represents a measurement of the antagonization of the effect induced by scopolamine which was brought about by the oral administration of the test substance.

A global analysis was carried out to evaluate the overall activity of the various test substances. A ranking series with respect to the performance improvement after the administration of the test substances compared with the test values obtained after the scopolamine injection over the six experimental conditions (test substances) was drawn up. The results obtained are presented as follows, the highest ranking total represents the best performance improvement:

| | | |
|---|---|---|
| Placebo | | 95 |
| Moclobemide | | 122.5 |
| Aniracetam | | 108.5 |
| 3-Hydroxyaniracetam | 750 mg | 94 |
| 3-Hydroxyaniracetam | 1500 mg | 95.5 |
| 3-Hydroxyaniracetam | 3000 mg | 93.5 |

We claim:

1. A method of treating cognitive disorders which comprises administering to a host requiring such treatment an effective amount of p-chloro-N-(2-morpholinoethyl)benzamide.

2. A method in accordance with claim 1, wherein the effective amount of p-chloro-N-(2-morpholinoethyl)-benzamide is in the range of from about 0.1 mg to about 20 mg per kg body weight.

3. A method in accordance with claim 2, wherein the cognitive disorder is caused by old age.

4. A method in accordance with claim 3, wherein the cognitive disorder is a hypomnesis.

5. A method in accordance with claim 2, wherein the cognitive disorder is a degenerative dementia.

6. A method in accordance with claim 5, wherein the cognitive dementia is a dementia of the Alzheimer type or a multi-infarct caused dementia.

* * * * *